US008764656B2

(12) United States Patent  
Shin et al.

(10) Patent No.: US 8,764,656 B2  
(45) Date of Patent: Jul. 1, 2014

(54) SENSING DEVICE OF EMOTION SIGNAL AND METHOD THEREOF

(75) Inventors: Hyun-Soon Shin, Daejeon (KR); Yong-Kwi Lee, Seoul (KR); Jun Jo, Daejeon (KR); Ji-Hoon Kim, Daejeon (KR); Jun-Sik Choi, Daejeon (KR); In-Tark Han, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 591 days.

(21) Appl. No.: 12/959,214

(22) Filed: Dec. 2, 2010

(65) Prior Publication Data

US 2011/0137137 A1 Jun. 9, 2011

(30) Foreign Application Priority Data

Dec. 8, 2009 (KR) ........................ 10-2009-0121185

(51) Int. Cl.  
*A61B 5/00* (2006.01)  
*G06F 3/01* (2006.01)

(52) U.S. Cl.  
CPC *G06F 3/01* (2013.01); *G06F 3/011* (2013.01); *G06F 3/012* (2013.01); *G06F 3/013* (2013.01); *G06F 3/014* (2013.01); *G06F 3/015* (2013.01); *G06F 3/016* (2013.01); *G06F 3/017* (2013.01)  
USPC ........................................................ 600/301

(58) Field of Classification Search  
None  
See application file for complete search history.

(56) References Cited

U.S. PATENT DOCUMENTS

| | | | | |
|---|---|---|---|---|
| 5,722,418 A | * | 3/1998 | Bro | 600/545 |
| 6,001,065 A | * | 12/1999 | DeVito | 600/544 |
| 6,607,484 B2 | * | 8/2003 | Suzuki et al. | 600/300 |
| 6,623,427 B2 | * | 9/2003 | Mandigo | 600/300 |
| 6,960,168 B2 | * | 11/2005 | Yanagidaira et al. | 600/300 |
| 8,185,380 B2 | * | 5/2012 | Kameyama | 704/10 |
| 8,204,786 B2 | * | 6/2012 | LeBoeuf et al. | 705/14.66 |
| 2006/0009702 A1 | * | 1/2006 | Iwaki et al. | 600/520 |
| 2007/0022074 A1 | * | 1/2007 | Muramatsu et al. | 706/50 |
| 2007/0192038 A1 | * | 8/2007 | Kameyama | 702/19 |
| 2008/0146890 A1 | * | 6/2008 | LeBoeuf et al. | 600/300 |
| 2008/0208015 A1 | * | 8/2008 | Morris et al. | 600/301 |
| 2008/0214903 A1 | | 9/2008 | Orbach | |
| 2009/0292528 A1 | * | 11/2009 | Kameyama | 704/9 |
| 2010/0234692 A1 | * | 9/2010 | Kuo et al. | 600/300 |

FOREIGN PATENT DOCUMENTS

| | | |
|---|---|---|
| JP | 2005-303722 A | 10/2005 |
| JP | 2008-532587 A | 8/2008 |
| KR | 1020070061054 A | 6/2007 |
| KR | 1020090032537 A | 4/2009 |
| KR | 1020090078889 A | 7/2009 |
| KR | 1020090081885 A | 7/2009 |

* cited by examiner

*Primary Examiner* — Gary Jackson  
*Assistant Examiner* — Shirley Jian (57) ABSTRACT

The present invention relates to a sensing device of an emotion signal and a method thereof capable of recognizing and analyzing the change in emotion by collecting at least one of the bio signals and peripheral environmental signals, guiding the state of emotion to a user, and sharing emotion information with authorized persons and communicating it between them. The sensing device of the emotion signal according to the embodiment of the present invention includes a sensing signal processor that senses a plurality of bio signals and peripheral environment signals of a user; an emotion signal processor that generates emotion signals representing the emotional state of the user for each of the sensed bio signals and collects the emotion signals to generate an emotion index; and an emotion signal communication unit that optionally transmits the emotion signals and the emotion index to external authorized devices.

16 Claims, 12 Drawing Sheets

SENSING DEVICE OF EMOTION SIGNAL AND METHOD THEREOF

CROSS REFERENCE TO RELATED APPLICATIONS

This application claims priority to Korean Patent Application No. 10-2009-0121185 filed on Dec. 8, 2009, the entire contents of which is herein incorporated by reference.

BACKGROUND OF THE INVENTION

1. Field of the Invention

The present invention relates to a sensing device of an emotion signal and a method thereof, and more particularly, to a sensing device of an emotion signal and a method thereof capable of recognizing and analyzing the change in emotion by collecting at least one of bio signals and peripheral environmental signals, guiding the state of emotion of a user, and sharing emotion information with authorized persons and communicating it between them.

2. Description of the Related Art

Recently, a need for a cognizing or recognizing technology as a method for intelligently determining and providing a user's intention and services in consideration of emotion and person's recognition aspect has been on the rise. By the above need, many researches have been conducted, but the emotion information service has not yet achieved the emotion recognition technology.

Society, in respects to the future, has a need for fulfilling a personal relationship and an aging society needs an emotion based service that can communicate emotion while being happy. In particular, a need exists for an emotion recognition technology, the emotion information exchange technology, etc., by recognizing bio signals and environmental signals when a user may be in an unrestricted and unresponsive state.

SUMMARY OF THE INVENTION

It is an object of the present invention to provide a sensing device of an emotion signal and a method thereof capable of extracting emotion signals by simply sensing at least one of bio signals and peripheral environmental signals in an unrestricted and unresponsive state and extracting the analyzing the sensed signals and determining and sharing the emotional state of the user.

It is another object of the present invention to provide an emotion based service by building a structure of a sensing device for sensing emotion signals, extracting the emotion signals according to the structure, and determining emotion index.

In order to achieve the above object, according to an exemplary embodiment of the present invention, there is provided a sensing device of an emotion signal, including: a sensing signal processor that senses a plurality of bio signals and peripheral environment signals of a user; an emotion signal processor that generates emotion signals representing the emotional state of the user for each of the sensed bio signals and collects the emotion signals to generate an emotion index; and an emotion signal communication unit that optionally transmits the emotion signals and the emotion index to external authorized devices.

The emotion signal processor may uses the emotion signals and the sensed peripheral environment signals to generate the emotion index.

The sensing signal processor may includes at least one of a PPG sensor, a GSR sensor, a temperature/humidity sensor, an acceleration sensor, a voice sensor, and an infrared sensor for unrestricted and unresponsive sensing.

The emotion signal processor may uses emotion changing threshold values that identify the emotion change of the user to extract the emotion signals from the bio signals.

The emotion signal processor may recognizes errors for each of the emotion signals using the motion signals together with the peripheral environment signals to generate the error recognition information and uses the error recognition information to perform the error compensation for each of the emotion signals.

The emotion signal processor may performs a multimodal convergence emotion inference using the emotion signals to determine the emotion index.

The emotion signal communication unit may shares the emotion signals with an external device needing the emotion signals themselves and shares the emotion index with an external device needing the emotion index.

The emotion signal communication unit may performs privacy security communication for privacy security for the emotional state of the user.

The sensing signal processor may include: a sensor unit that has a plurality of sensors sensing the bio signals and the peripheral environment signals; an amplifier that amplifies signals input from the plurality of sensors; a noise filtering unit that removes external noise from the amplified signals; an analog/digital interface (I/F) unit that converts the output signals from the noise filtering unit into a digital signal; and a digital signal output unit that outputs the digital signals.

The emotion signal processor may includes: an emotion signal threshold generation and control unit that identifies the change in emotion of the user and manages the change in the emotion changing threshold values; an emotion signal extractor that extracts the emotion signals representing the emotional state of the user for each of the sensed bio signals by using the emotion changing threshold values; an emotion signal error state recognizer that analyzes the peripheral environment signals and the motion signals to perform the error state recognition for each of the emotion signals; an emotion signal compensator that compensates and optimizes the corresponding emotion signal according to the error state recognition; an emotion index inference unit that performs the emotion inference on the emotion signals and the peripheral environment signals as an input to infer the emotion index; and an emotion signal information managing unit that manages the emotion signals and the emotion index.

The emotion signal communication unit may includes: an emotion signal information formatting processor that formats the emotion signals and provides them to the peripheral devices and terminals; an emotion signal security processor that performs security processing for privacy security for the emotional state of the user; an emotion signal communication protocol processor that processes protocols for the emotion signal communication; and an emotion signal communication matching unit that matches wireless signals with the emotion signal communication.

The sensing device of an emotion signal may further include a hardware (H/W) controller that provides a platform for executing the sensing signal processor, the emotion signal processor, and the emotion signal communication unit, wherein the H/W controller includes: a sensor analog interface unit that receives the analog signals from the plurality of sensors; a main signal processor that in charge of the booting of the plurality of sensors and execute of the software (SW) module; a low power unit that provides a low power service; and a wireless communication module that performs the emotion signal wireless communication.

According to another exemplary embodiment of the present invention, there is provided a sensing method of an emotion signal, including: sensing a plurality of bio signals and peripheral environment signals of a user by a sensing signal processor; generating emotion signals representing the emotional state of the user from each of the bio signals sensed by the emotion signal processor and collects the emotion signals to generate the emotion index; and optionally providing the emotion signals and the emotion index to the external authorized devices by the emotion signal communication unit.

The sensing performs sensing may uses at least one of a PPG sensor, a GSR sensor, a temperature/humidity sensor, an acceleration sensor, a voice sensor, and an infrared sensor for unrestricted and unresponsive sensing.

The generating of the emotion index may generates the emotion index using the emotion signals and the sensed peripheral environment signals.

The generating the emotion index may includes: generating the emotion changing threshold values that identifies the change in emotion of the user; and extracting the emotion signals from the bio signals using the emotion changing threshold values.

The generating the emotion index may generates the error recognition information by recognizing the error state based on the peripheral environment signals and the motion signal and performs error compensation on each of the emotion signals using the error recognition information.

The generating the emotion index may determines the emotion index by performing the convergence emotion inference using the emotion signals in the finally compensated multimodal manner.

The external authorized devices may shares the emotion signals when it is an external device needing the emotion signals and shares the emotion index when it is an external device needing the emotion index.

The external authorized devices may performs privacy security management and privacy security communication for privacy security for the emotional state of the user.

According to an exemplary embodiments of the present invention, it can simply sense at least one of the bio signals and peripheral environmental signals in unrestricted and unresponsive state and extracting the emotion signals by analyzing the sensed signals, thereby determining the emotional state of the user in the unrestricted state and providing the emotional state and providing the emotion service in order to meet the user's emotion.

Further, the present invention provides the emotion signals to the user and his family, thereby making it possible to provide services that communicate the emotion therebetween.

DETAILED DESCRIPTION OF THE PREFERRED EMBODIMENTS

Hereinafter, exemplary embodiments of the present invention will be described with reference to the accompanying drawings.

Figure 1:
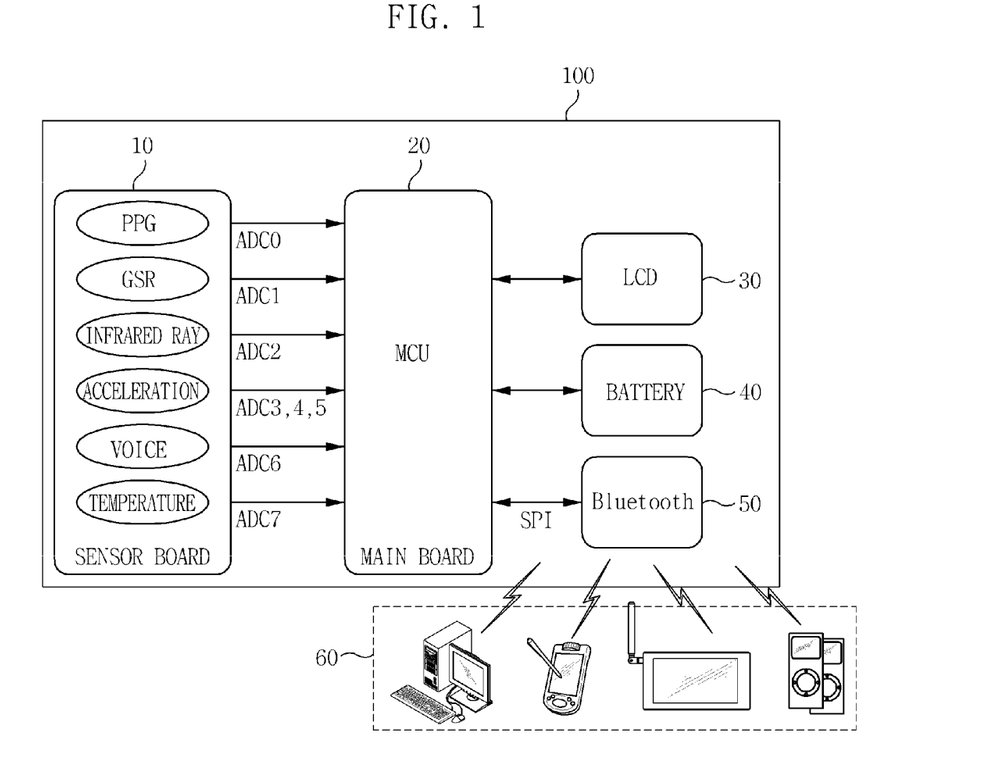
FIG. 1 is a diagram showing an example of a system to which a sensing device of an emotion signal according to an exemplary embodiment of the present invention is applied.

FIG. 1 is a diagram showing an example of a system to which a sensing device of an emotion signal according to an exemplary embodiment of the present invention is applied (non-explained reference numerals ADC0 to ADC7 are signal lines and SPI is a communication line).

Referring to FIG. 1, a sensing device 100 of an emotion signal may be applied to a sensing based emotion service device. In particular, it is configured to extract emotion signals from at least one of bio signals of a user. For example, the sensing device of the emotion signal may be configured to process various sensing signals from a sensor board 10 including various sensors in a microcomputer unit (MCU), etc., and display the emotion signals or the emotion indices on a display unit 30 (LCD) or share them with external devices 60 (a computer, an MP3, a cellular phone, a PDA, etc.) through the communication unit 50 (Bluetooth, etc.). Of course, it may be configured to be carried by including a battery 40 therein (for example, a necklace, a pendent, an MP3, a cellular phone, a PDA, etc.). In other words, the present invention senses at least one of the bio signals and peripheral environmental signals, thereby making it possible to recognize and analyze the change in emotion, guide the state of emotion to the user, and share the emotion information between authorized persons. The change in emotion means the change in an emotional state of the user (for example, serenity, angry, astonishment, sadness, etc.).

Hereinafter, the configuration of the sensing device 100 of the sensing based emotion signal according to the embodiment of the present invention will be described in more detail.

Figure 2:
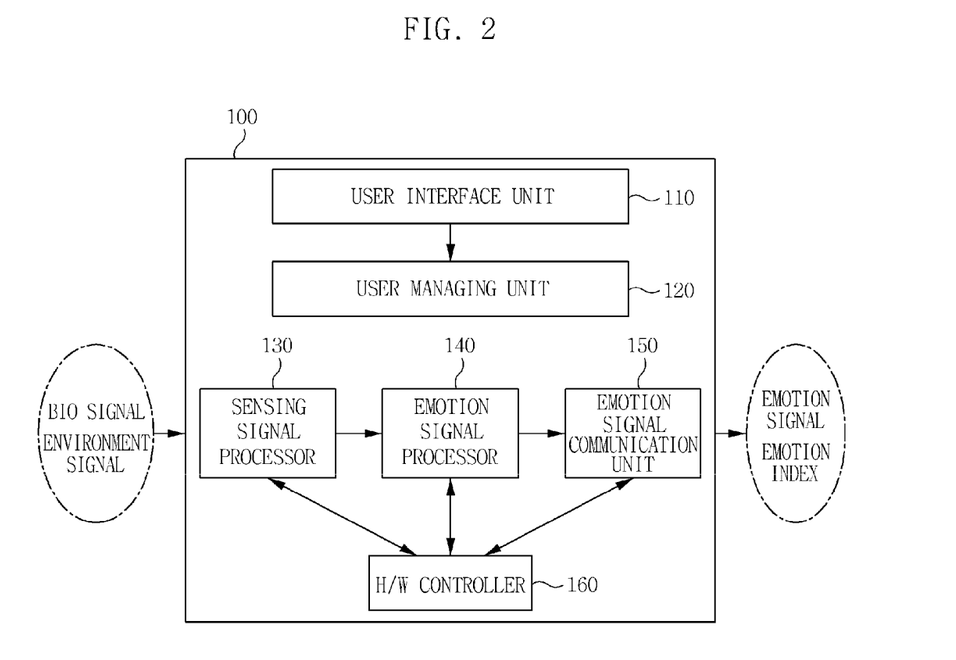
FIG. 2 is diagram showing an internal configuration of a sensing device of an emotion signal according to the exemplary embodiment of the present invention.

FIG. 2 is diagram showing an internal configuration of a sensing device of an emotion signal according to the exemplary embodiment of the present invention and FIGS. 3 to 6 are diagrams schematically showing a detailed configuration of the sensing device of the emotion signal shown in FIG. 2.

Referring to FIG. 2, the sensing device 100 of the emotion signal according to the embodiment of the present invention is configured to include a sensing signal processor 130, an emotion signal processor 140, an emotion signal communication unit 150, and a hardware (H/W) controller 160.

Briefly describing the sensing device of the emotion signal according to the present invention, the sensing signal processor 130 senses at least one of the bio signals and peripheral environmental signals for the user. The emotion signal processor 140 generates the emotion signals representing the emotional state of the user for each of at least one of the bio signal and collects the emotion signals to generate the emotion index.

Further, the emotion signal processor 140 generates the emotion index using the emotion signals and the processed peripheral environmental signals. The emotion signal communication unit 150 optionally provides the emotion signals and the emotion index to the outside to be shared with authorized devices and users. The H/W controlling unit 160 controls a H/W platform that can execute the sensing processing, the emotion signal processing, and the emotion signal communication processing, and so on. The configuration of the sensing device of the emotion signals according to the exemplary embodiment of the present invention will be described in detail.

In other words, the present invention senses at least one of the bio signals and peripheral environmental signals, thereby making it possible to recognize and analyze the change in emotion, guide the state of emotion to the user, and share the emotion information between authorized persons. As a result, the present invention may inform the users of the emotional state of a person and communicate the emotion between the users.

Further, the sensing device of the emotion signal according to the exemplary embodiment of the present invention may further include a user interface unit 110 (UI) and a user managing unit 120. The user interface unit 110 serves to guide the emotion signal and the emotion index to be described below (S267) and provide the emotion services meeting a person. The user managing unit 120 serves to manage the user that provides the user emotion signal and emotion index to be described below. In other words, the user managing unit 120 performs authentication processing so that authorized persons can share the emotion signal or the emotion index representing the emotional state of the user. The user authorizing and providing scheme is known and therefore, the detailed description thereof will be omitted.

Figure 3:
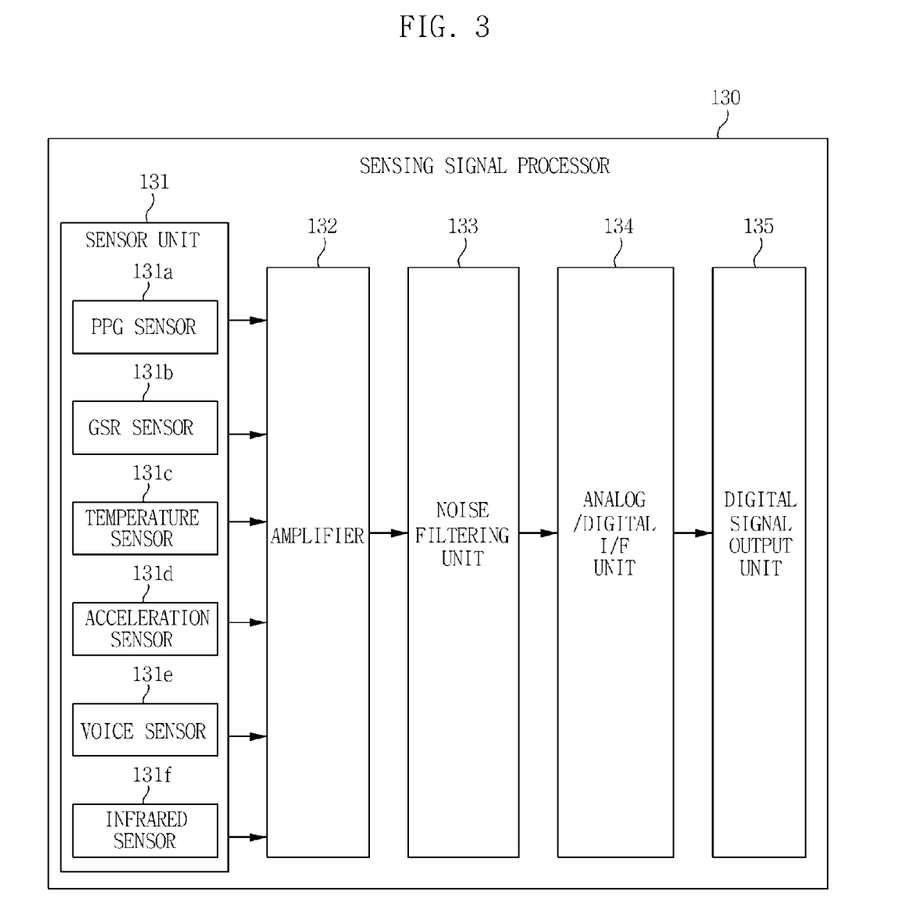
FIGS. 3 to 6 are diagrams schematically showing a detailed configuration of the sensing device of the emotion signal shown in FIG. 2.

Referring to FIG. 3, the sensing signal processor 130 is configured to include a sensor unit 131 (multimodal scheme), an amplifier 132, an analog/digital interface (I/F) unit 134, and a digital signal output unit 135. The sensor unit 131 is configured to include at least one sensor for performing the unrestricted and unresponsive sensing such as a PPG sensor 131*a*, a GSR sensor 131*b*, a temperature sensor 131*c*, an acceleration sensor 131*d*, a voice sensor 131*e*, an infrared sensor 131*f*, etc. The sensor unit 131 senses at least one of the bio signals and peripheral environmental signals of a user through at least one of the sensors 131*a* to 131*f*. The amplifier 132 amplifies signals input from the sensors. A noise filtering unit 133 removes external noise from the amplified signals. The analog/digital I/F unit 134 converts analog signals into digital signals. The digital signal output unit 135 outputs digital signals converted to analyze the bio signals. Each component of the sensing signal processor 130 adopts a configuration to sense and process the bio signals and peripheral environmental signals of the user but is not limited thereto.

The sensing signal processor 130 processes the sensed signals by the multimodal scheme and provides them to analyze the emotional state of the user in the emotion signal processor 140. The acceleration sensor 131*d* can recognize whether the emotion of the user is due to exercise or the change in emotion. The sensed signals is processed as the analyzable signals by passing through the amplifier 132, the noise filtering unit 133, the analog/digital I/F unit 134, and the digital signal output unit 135. The above-mentioned multimodal scheme is known and therefore, the more detailed description thereof will be described.

Figure 4:
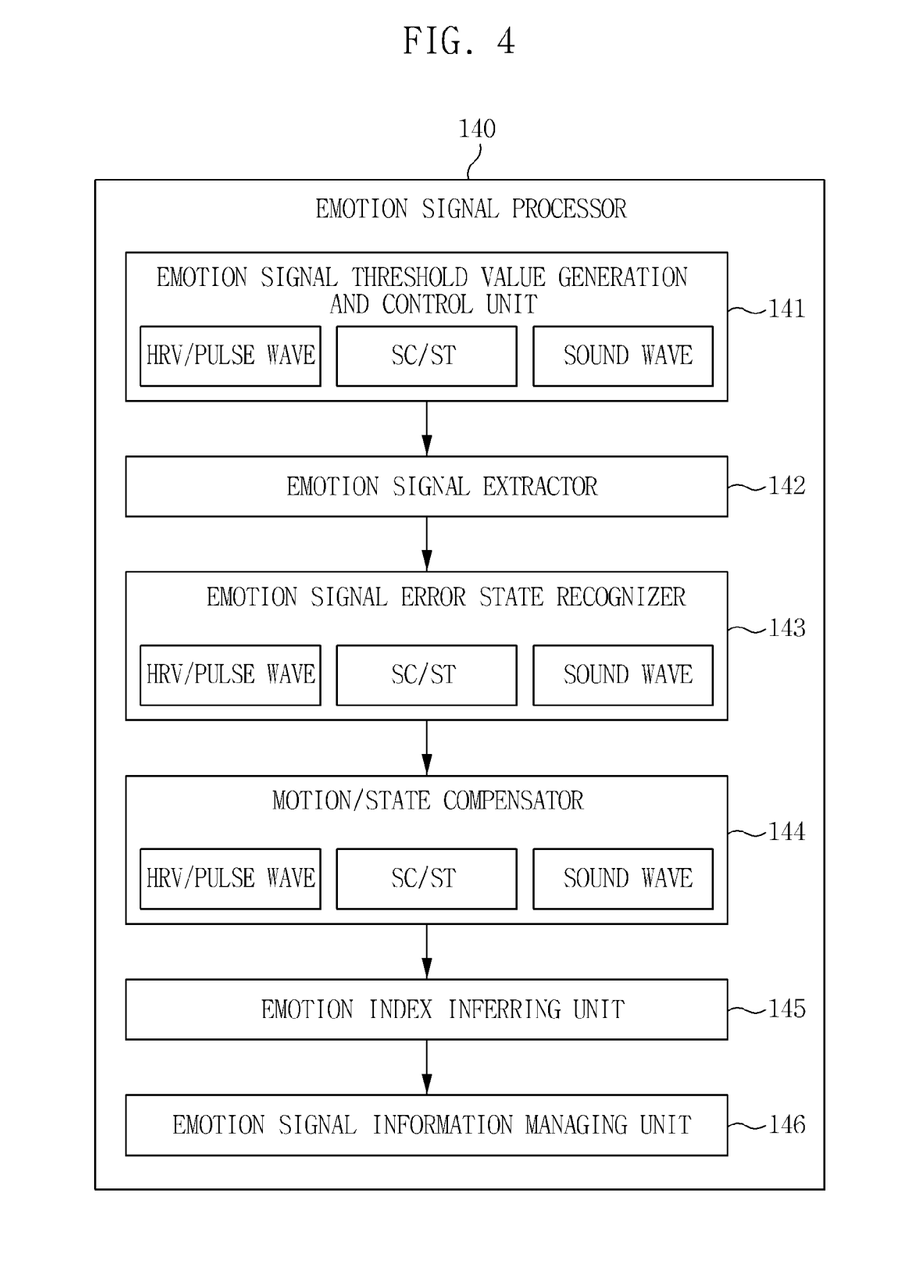

Referring to FIG. 4, the emotion signal processor 140 is configured to include an emotion signal threshold generation and control unit 141, an emotion signal extractor 142, an emotion signal error state recognizer 143, an emotion signal compensator 144, an emotion index inferring unit 145, and an emotion signal information managing unit 146.

The emotion signal threshold generation and control unit 141 processes a reference value to determine the change in emotion of the user from signals sensed and processed in the above-mentioned sensing signal processor 130. In other words, the emotion signal threshold generation and control unit 141 generates a threshold value for the emotion signal that can identify the change in emotion and manages the change in the generated threshold value. The emotion signal extractor 142 extracts the emotion signal based on the threshold value. The emotion signal error state recognizer 143 analyzes the peripheral environment signals to recognize the error state. The emotion signal compensator 144 performs the emotion signal optimization according to the recognition of the emotional signal error state. The emotion index inferring unit 145 performs the emotion inference using the emotion signals and the peripheral environment signals as an input. The emotion signal information managing unit 146 manages the extracted emotion signals and the feedback emotion signal state information, etc.

Figure 5:
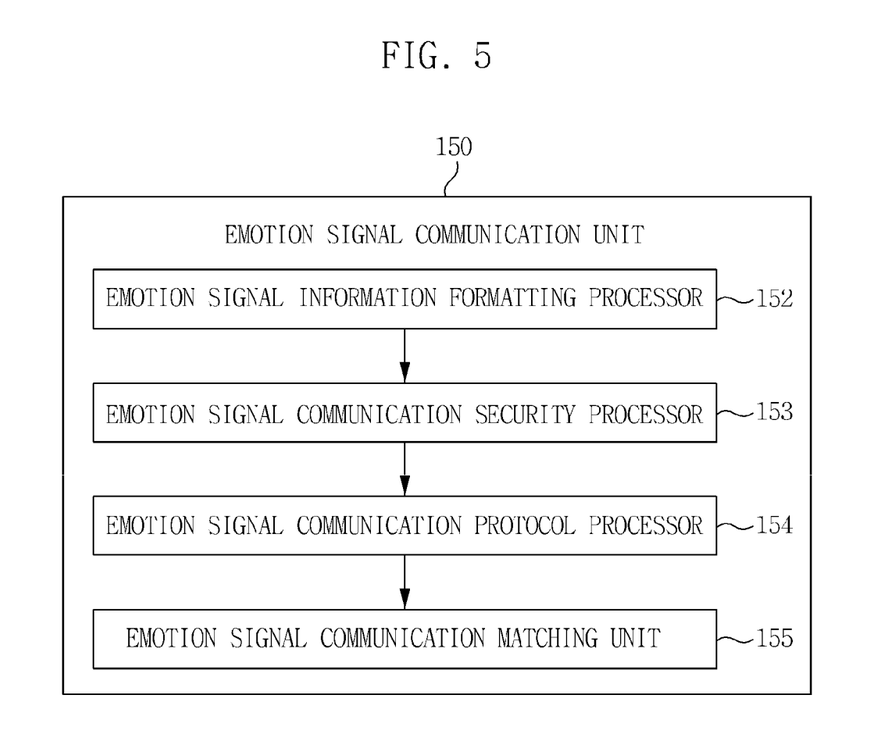

Referring to FIG. 5, the emotion signal communication unit 150 is configured to include an emotion signal information formatting processor 152, an emotion signal security processor 153, an emotion signal communication protocol processor 154, and an emotion signal communication matching unit 155.

The emotion signal information formatting processor 152 prepares the emotion signal communication message in order to provide at least one of the emotion signals to the peripheral devices and terminals. The emotion signal security processor 153 processes privacy security for the emotion signal information of a person. The emotion signal communication protocol processor 154 processes the protocols for emotion signal communication. The emotion signal communication matching unit 155 processes wireless emotion signal communication.

Figure 6:
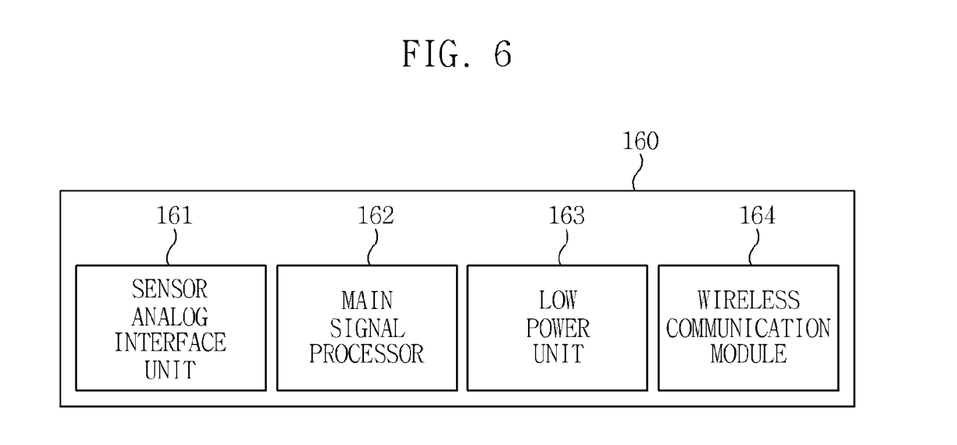

Referring to FIG. 6, the H/W controller 160 is configured to include a sensor analog interface unit 161, a main signal processor 162, a low power unit 163, a wireless communication module 164.

The sensor analog interface unit 161 receives the analog signals from various sensors. The main signal processor 162 is in charge of a booting of a sensor device and execution of a software (SW) module. The low power unit 163 provides the low power service. The wireless communication module 164 executes the emotion signal wireless communication.

However, the method for sensing the emotion signal according to the exemplary embodiment of the present invention will be described with reference to the accompanying drawings. In the description, an example of the sensing device of the emotion signal having the above-mentioned configuration will be described by way of example. Further, the sensing device of the emotion signal may be configured to be connected on the system to sense the bio signals and the environment signals.

Figure 7:
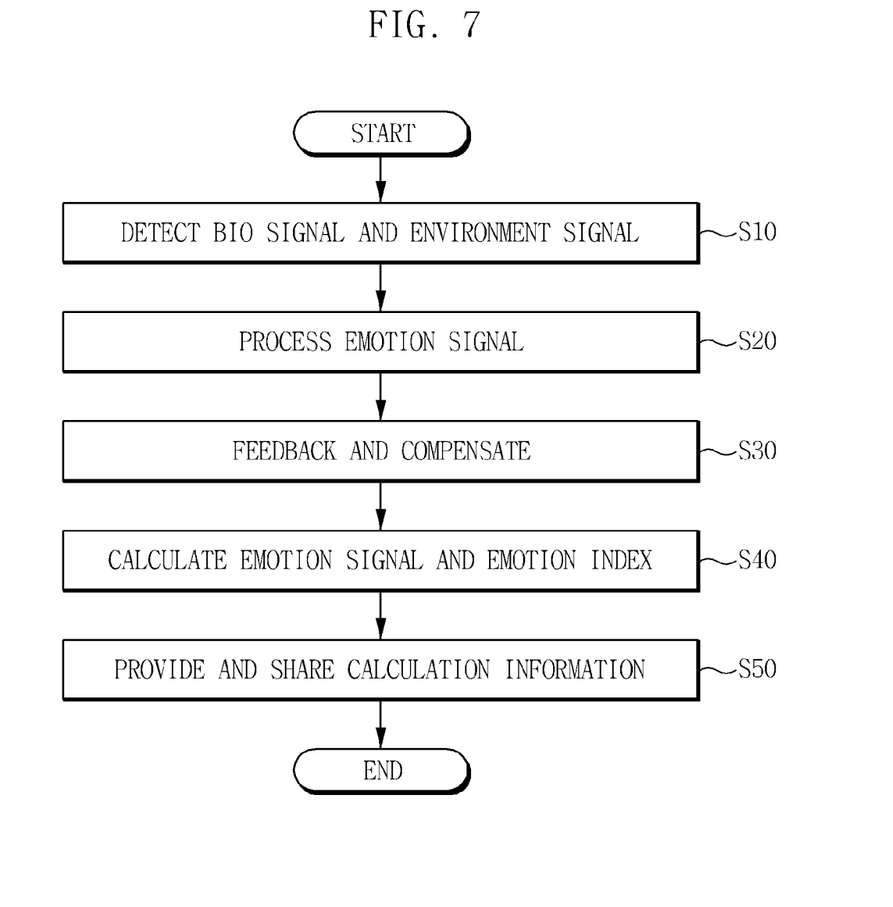
FIG. 7 is a diagram showing a sequence of a sensing method of an emotion signal according to the exemplary embodiment of the present invention.

FIG. 7 is a diagram showing a sequence of the sensing method of emotion signal according to the exemplary embodiment of the present invention. In the description, an example of the sensing device of the emotion signal having the above-mentioned configuration will be described by way of example.

Referring to FIG. 7, when the sensing device 100 of the emotion signal according to the present invention is used by the user, the sensing signal processor 130 senses at least one of the bio signals and peripheral environment signals for the user and processes them as the analyzable signals (S10).

Next, the emotion signal processor 140 processes various signals (that is, signals processed from the sensed bio signals and peripheral environment signals) from the sensing signal processor 130 and processes them as the emotion signals representing the emotional state of the user (S20). The emotion signal processor 140 generates the emotion changing threshold value that can identify the change in emotion of the user and uses it to extract each emotion signal from at least one of the bio signals.

Then, in order to optimize the emotion signal, the feedback and compensation functions are performed. In other words, the emotion signal processor 140 performs error compensation on the emotion signals by using the peripheral environmental signals to reduce the errors.

Next, the emotion signal processor 140 determines the emotion index through the convergence inference by using the emotion signals and the peripheral environment signals.

Finally, the determined emotion signals or the emotion index are provided to the user in the user interface and the wireless communication. In other words, the emotion signal communication unit 150 shares the emotion signals if it is the external device requiring the emotion signal itself. In addition, the emotion signal communication unit 150 shares the emotion index if it is not the external device requiring the emotion signal itself.

As described above, the present invention simply senses at least one of the bio signals and peripheral environment signals in the unrestricted and unresponsive state and analyzes the sensed signals to extract the emotion signals, thereby grasping the emotional state of a person in the unrestricted state and providing the emotion state and providing the emotion service meeting the emotion of a person. Of course, the present invention provides the emotion signals to the user and his family, thereby making it possible to provide services that can communicate the emotion.

Hereinafter, a process of processing and communicating the emotion signal according to the sensing device of the emotion signal according to the embodiment of the present invention will be described by way of example.

FIGS. 8 to 13 are diagrams showing a sequence of a process for processing and communicating the sensing based emotion signal in the sensing device of the emotion signal according to the exemplary embodiment of the present invention.

An example of a sensing and processing process of the sensing device of the emotion signal according to the exemplary embodiment of the present invention will be described with reference to FIGS. 8 to 13.

Figure 8:
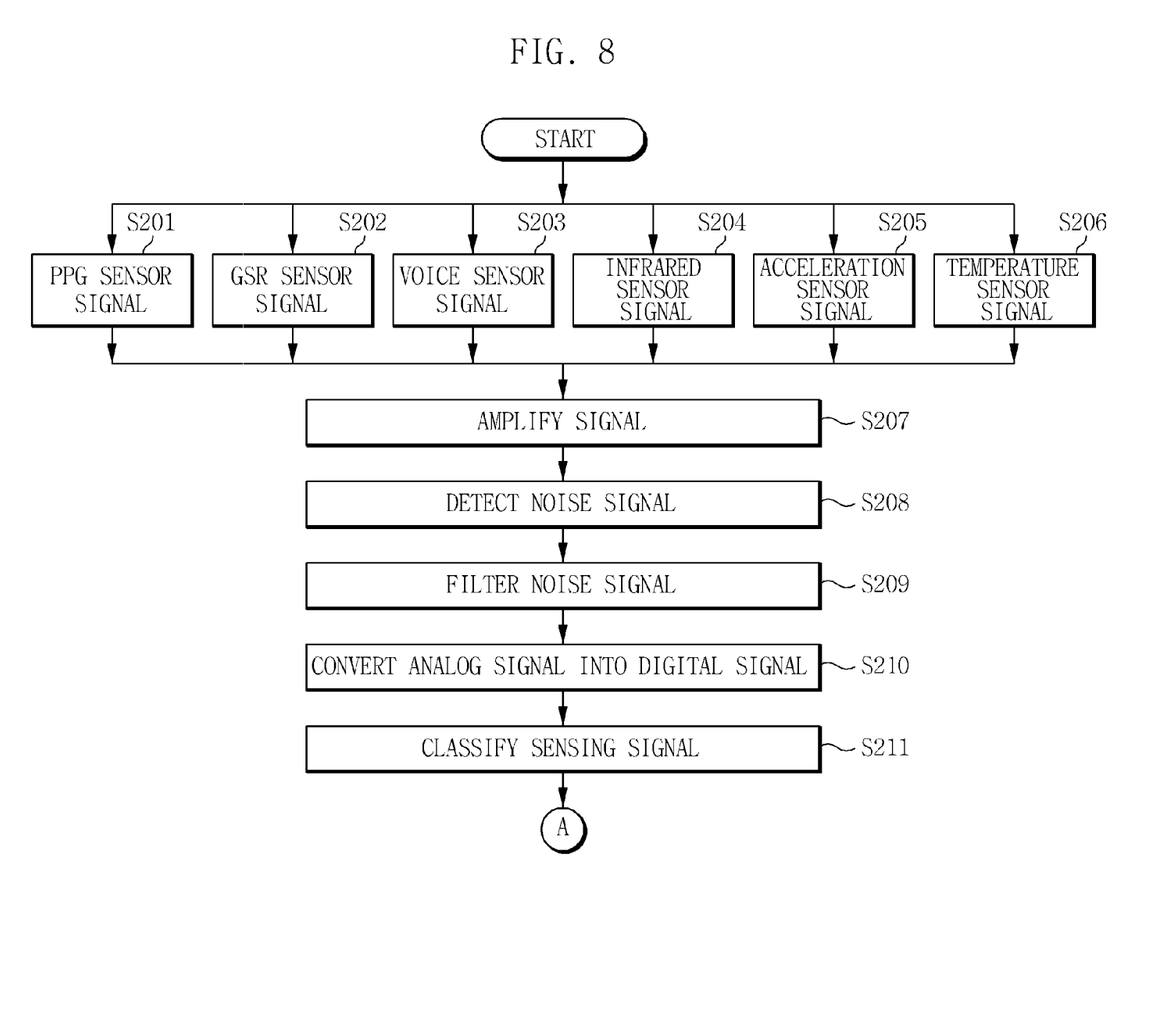
FIGS. 8 to 13 are diagrams showing a sequence of a process of processing and communicating a sensing based emotion signal in the sensing device of the emotion signal according to the exemplary embodiment of the present invention.
Figure 9:
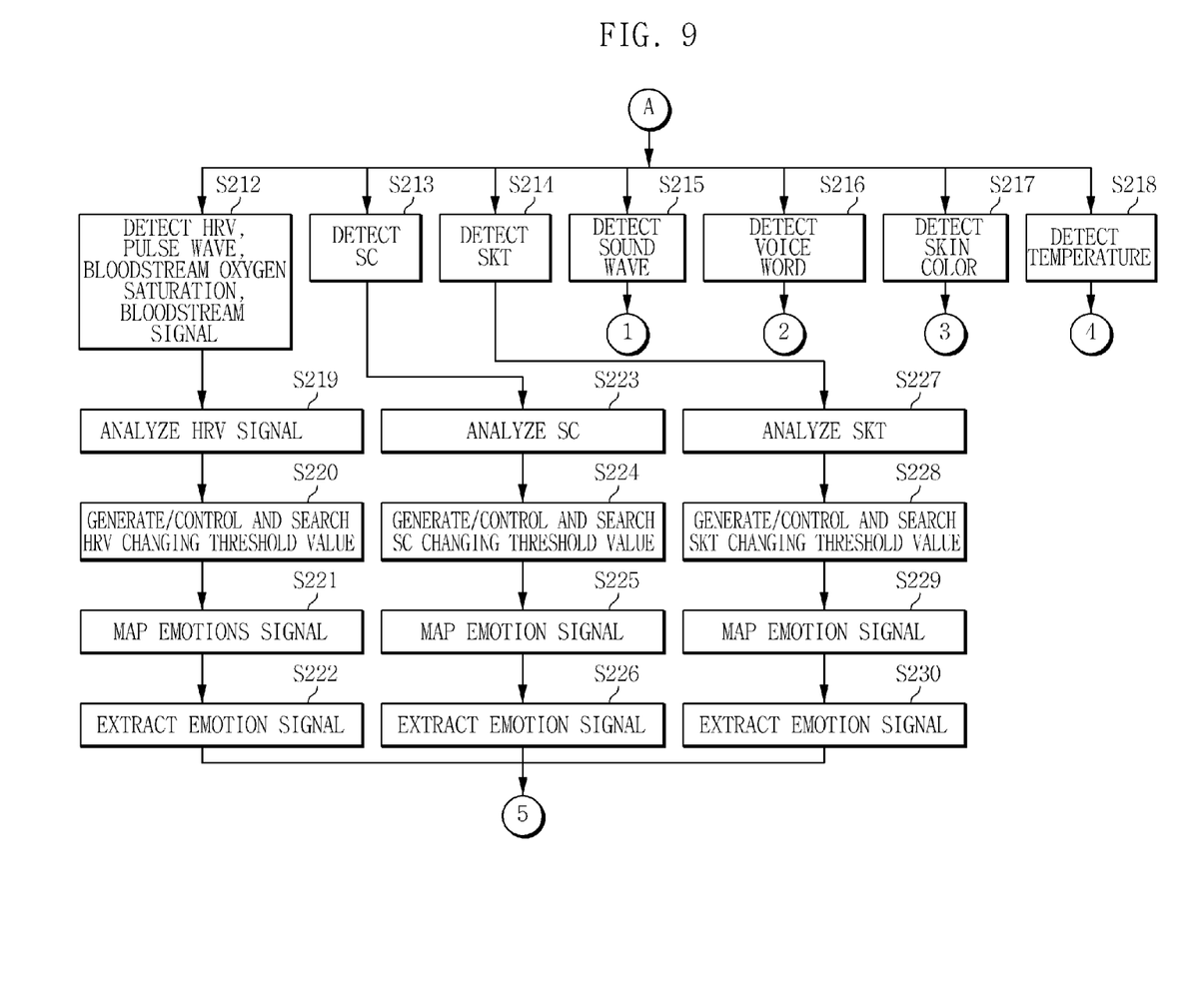
Figure 10:
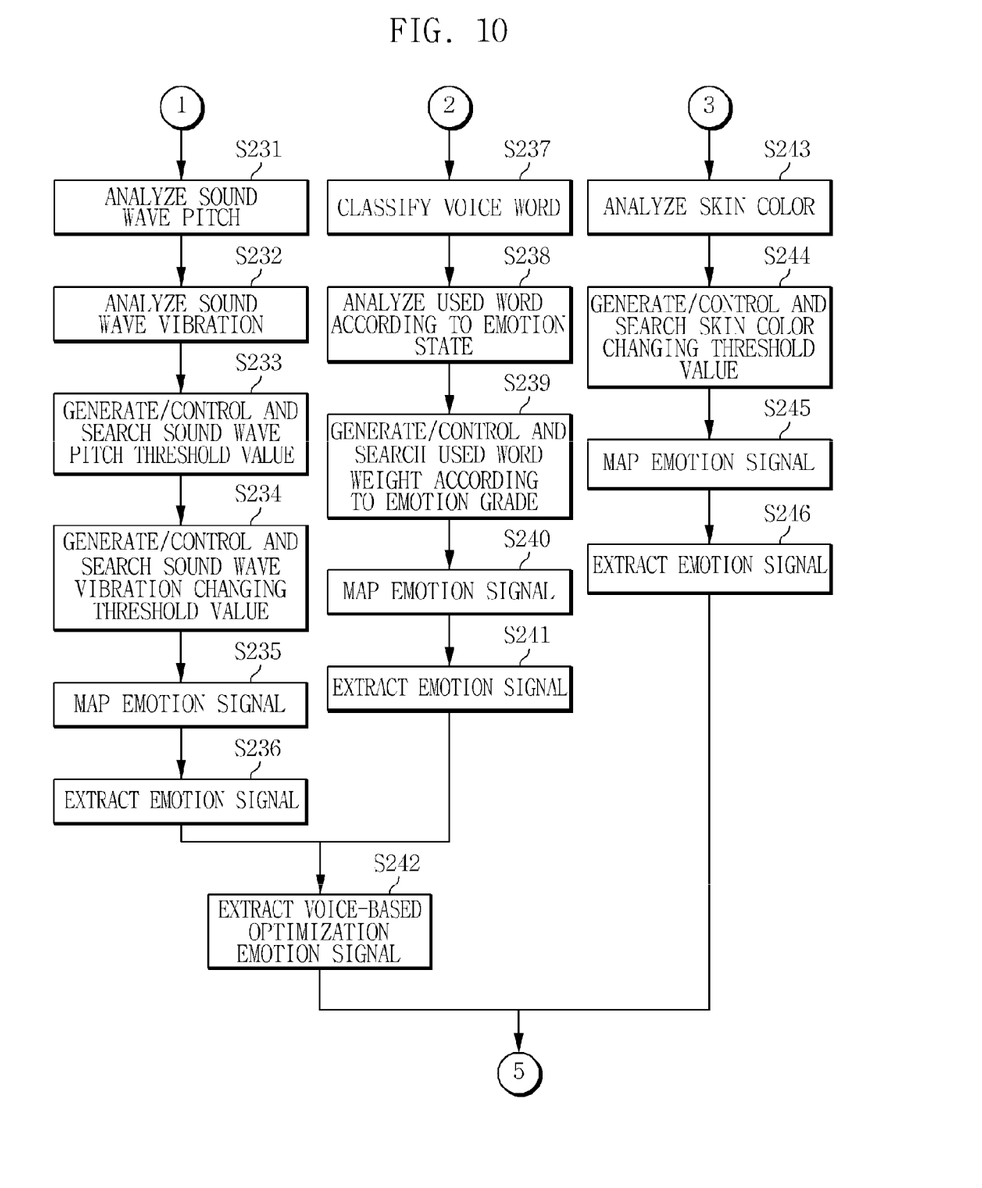
Figure 11:
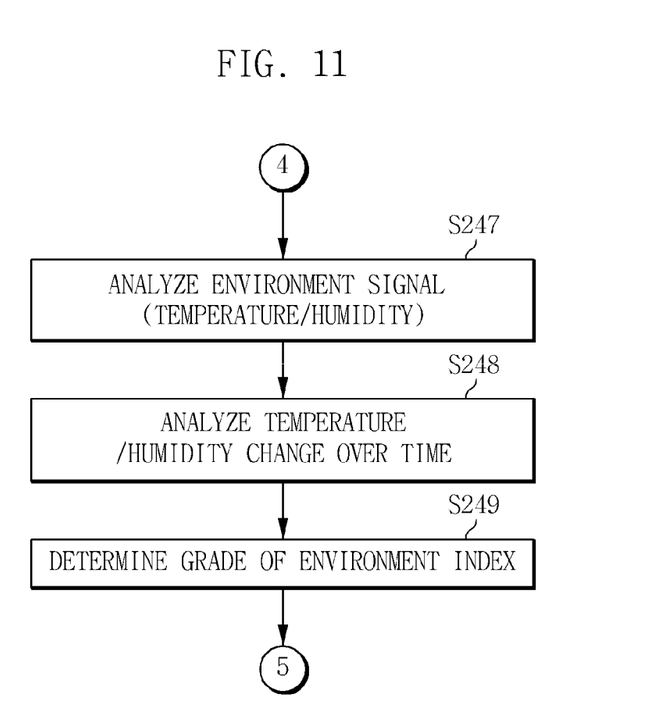
Figure 12:
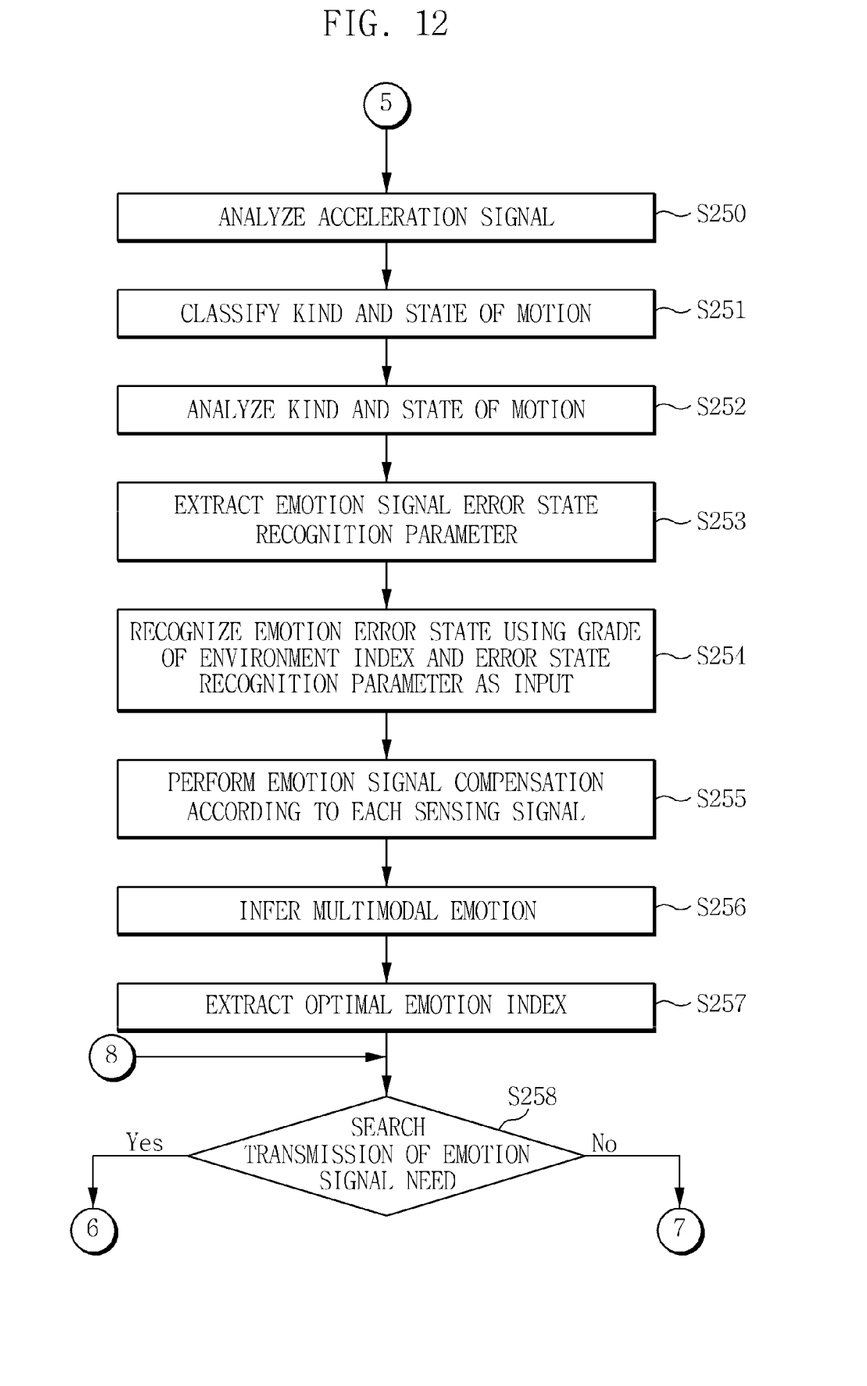
Figure 13:
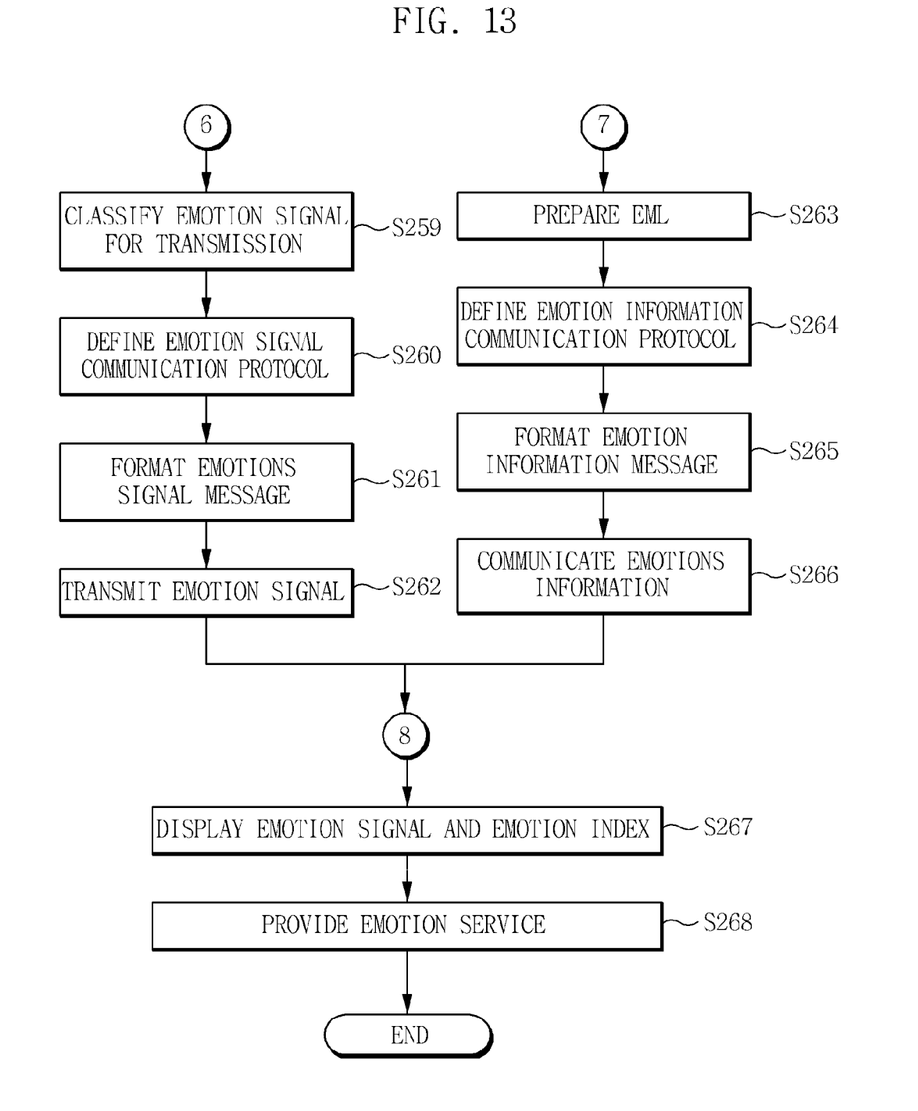

First, the sensor unit 131 in the sensor signal processor 130 detects the bio signals by a method for detecting reflected and transmitted light by irradiating light having a specific wavelength band from the PPG sensor 131a for performing unrestricted and unresponsive signal sensing in the sensor unit 131 (201), measures body temperature for recognizing the skin resistance and the change in body temperature using the GSR sensor 131b (S202), recognizes voice using a voice sensor 131e (mic) (S203), senses colors and convulsion of skin using the infrared sensor 131f (S204), measures motion and quantity of motion, etc., using the acceleration sensor 131d (S205), and measures temperature (or humidity) in the environment using a temperature sensor 131c (or a humidity sensor (not shown)) (S206).

After step 'S206', the amplifier 132 amplifies the bio signals in order to reinforce a sensed bio signal (S207).

After performing step 'S207', the noise filtering unit 133 extracts signals meeting each band and extracts the noise signals (S208), thereby filtering the noise through a notch filter (S209).

After performing step 'S209', the analog/digital I/F unit 134 converts 6 analog bio signals into digital signals (S210), thereby classifying each digital bio signal (S211).

After step 'S211', the emotion signal processor 140 detects an HRV, a pulse wave, blood stream oxygen saturation, a strength signal of blood stream, etc. (S212) from the signal sensed the PPG sensor 131a, thereby analyzing the HRV, the pulse wave, the blood stream oxygen saturation, the strength signal of blood stream, and so on (S219).

After step 'S219', the emotion signal processor 140 generates/controls and searches an HRV changing threshold value, a pulse wave changing threshold value, an oxygen saturation changing threshold value, and a blood stream strength changing threshold (S220) and maps the emotion signals according to the grade of the threshold values (S221), thereby extracting the PPG-based emotion signal (S222). Herein, it is considered that generating/controlling and searching the threshold value includes generating the threshold value or controlling the existing threshold value according to a newly generated threshold value and searching the threshold values by a comparison scheme, etc. Hereinafter, it is considered that the scheme of generating/controlling and searching the threshold values may use the known methods.

Meanwhile, after performing step 'S211', the emotion signal processor 140 detects an electrical conductivity (SC) signal from a sensed signal using the GSR sensor 131b (S213), thereby analyzing the skin electrical conductivity (S223).

After performing step 'S223', the emotion signal processor 140 generates/controls and searches the skin electrical conductivity changing threshold value according to the change in emotion (S224) and maps the emotion signal according to the grade of the threshold value (S225), thereby extracting the SC change-based emotion signal (S226).

Further, after performing step 'S211', the emotion signal processor 140 detects a skin body temperature (SKT) from a sensed signal using the infrared sensor 131f (body temperature sensor) (S214), thereby analyzing the change in the skin body temperature (S227).

After performing step 'S227', the emotion signal processor 140 generates/controls and searches the skin body temperature changing threshold value according to the change in emotion (S228) and maps the emotion signal according to the grade of the threshold value (S229), thereby extracting the SKT change-based emotion signal (S230).

Further, after performing step 'S211', the emotion signal processor 140 detects a sound wave forming voice (S215), analyzes the pitch change of sound (S231), and analyzes the vibration change between pitches (S232).

After performing step 'S232', the emotion signal processor 140 generates/controls and searches the pitch changing threshold value of sound according to the change in emotion (S233), generates/controls and searches the changing threshold value of the vibration (S234), and maps the emotion signal according to the grade of the threshold value (S235), thereby extracting the voice strength change-based emotion signal (S236).

Meanwhile, after performing step 'S211', the emotion signal processor 140 detects voice words (S216) and classifies voice words (S237), thereby classifying the used words (S238).

After performing step 'S238', it searches the used words according to the grade of the emotion index (S239), maps the emotion signal according to the grade of the emotion index (S240), and extracts the voice word-based emotion signal (S241).

After performing step 'S241', the emotion signal processor 140 analyzes and processes the sound wave analysis-based emotion signal and the voice word-based emotion signal, thereby extracting the voice-based optimized emotion signal (S242).

In addition, after performing step 'S211', the emotion signal processor 140 detects a skin color (S217), thereby analyzing the change in skin color (S243).

After performing step 'S243', the emotion signal processor 140 generates/controls and searches the skin color change according to the change in emotion (S244) and maps the emotion signal according to the grade of the threshold value (S245), thereby extracting the skin color change-based emotion signal (S246).

Further, after performing step 'S211', the emotion signal processor 140 detects the temperature (or humidity) information in the environment sensed from the temperature sensor 131*c* (or a humidity sensor) (S218) and analyzes the change in temperature (or humidity) in the environment (S247).

After performing step 'S247', the emotion signal processor 140 searches the temperature change over time (S248), thereby determining the environment index level (grade) (S249).

Meanwhile, after performing steps 'S201' to 'S249', the emotion signal processor 140 analyzes the acceleration sensing information using the acceleration sensor 131*d* (S250), thereby classifying the kind and state of motion (S251).

After performing 'S251', the emotion signal processor 140 analyzes the kind and state of motion (S252), thereby extracts parameters for recognizing the error state (S253).

After performing step 'S253', the emotion signal processor 140 uses the environment index level determined during steps 'S247' to 'S249' and the motion error state information extracted during steps 'S252' to 'S253' as the input to perform the emotion signal error state recognition algorithm, thereby recognizing the emotion signal error state (S254).

After performing step 'S254', the emotion signal processor 140 performs a process of compensating the emotion signal extracted from PPG, GSR, infrared ray, voice, and temperature/humidity signals that are extracted based on the recognized error state information (S255).

After performing step 'S255', the emotion signal processor 140 uses the compensated multimodal emotion signals to perform the multimodal convergence emotion inference (S256), thereby determining the optimal emotion index (S257).

After performing step 'S257', the emotion signal communication unit 150 searches whether there is a need to transmit the emotion signal itself (S258) to define and classify the emotion signal to be transmitted, in order to transmit it to the emotion service terminals or devices needing the compensated multimodal sensing signal-based emotion signal itself through the emotion signal communication unit 150 when the transmission of the emotion signal itself is needed (S259). The emotion signal communication unit 150 defines each emotion signal as the emotion signal communication protocol (S260) and formats in order to meet the emotion signal communication message format (S261), thereby transmitting it by using the wireless communication function (S262).

After performing step 'S257', the emotion signal communication unit 150 represents the extracted emotion index as an emotional markup language (EML) when there is no need to transmit the emotion signal itself (S263). The emotion signal communication unit 150 defines the emotion information communication protocol (S264) and formats in order to meet the emotion information communication message format (S265), thereby transmitting it by using the wireless communication function (S266).

Meanwhile, after performing step 'S257' or 'S262' or 'S266', it guides the emotion signal and the emotion index through the user interface unit 110 (UI) (S267) and provides the emotion service meeting the need of a person (S268).

Accordingly, the sensing device of the emotion signal and the method thereof disclosed in the present invention will be described with reference to the accompanying drawings but are used not to limit to the specific embodiments. The scope of the present invention is not limited only to the embodiments and the accompanying drawings. The protection scope of the present invention must be analyzed by the appended claims and it should be analyzed that all spirits within a scope equivalent thereto are included in the appended claims of the present invention.

What is claimed is:

1. An emotion sensing device, the device comprising:
   a sensing signal processor configured to sense a plurality of bio signals of a user and peripheral environment signals of a user;
   an emotion signal processor configured to generate an emotion signal associated with an emotional state of the user for each of the sensed bio signals, and collect the emotion signals to generate an emotion index; and
   an emotion signal communication unit configured to transmit any of the emotion signals and the emotion index to an external authorized device,
   wherein the emotion signal processor is configured to generate error recognition information for the emotion signals using the peripheral environment signals, and use the error recognition information to recognize an error for the emotion signals and perform error compensation.

2. The sensing device according to claim 1, wherein the emotion signal processor uses the emotion signals and the sensed peripheral environment signals to generate the emotion index.

3. The sensing device according to claim 1, wherein the sensing signal processor includes at least one of a PPG sensor, a GSR sensor, a temperature/humidity sensor, an acceleration sensor, a voice sensor, and an infrared sensor.

4. The sensing device according to claim 1, wherein the emotion signal processor is configured to use an emotion changing threshold value to identify an emotion change of the user, and generate an emotion signal corresponding to a sensed bio signal by using the emotion changing threshold value to extract the emotion signal from the bio signal.

5. The sensing device according to claim 1, wherein the emotion signal processor is configured to perform a multimodal convergence emotion inference using the emotion signals to determine the emotion index.

6. The sensing device according to claim 1, wherein the emotion signal communication unit is configured to perform a privacy security process before transmitting the emotion signals or the emotion index to the external authorized device.

7. The sensing device according to claim 1, wherein the sensing signal processor includes:
   a sensor unit including a plurality of sensors configured to sense the bio signals and the peripheral environment signals;
   an amplifier configured to amplify signals input from the plurality of sensors;
   a noise filtering unit configured to remove external noise from the amplified signals;
   an analog/digital I/F unit configured to convert the output signals from the noise filtering unit into digital signals; and
   a digital signal output unit configured to output the digital signals.

8. The sensing device according to claim 7, further comprising a hardware (H/W) controller configured to provide a platform for the sensing signal processor, the emotion signal processor, and the emotion signal communication unit, and
   wherein the H/W controller includes:
   a sensor analog interface unit configured to receive analog signals from the plurality of sensors;

a main signal processor configured to control booting of a software (SW) module associated with the plurality of sensors and execution of the SW module;

a low power unit configured to provide a low power service; and a wireless communication module configured to perform emotion signal wireless communication.

9. The sensing device according to claim 1, wherein the emotion signal processor includes:

an emotion signal threshold generation and control unit configured to generate a plurality of emotion changing threshold values to identify a change in emotion of the user, and manage a change in the generated emotion changing threshold values;

an emotion signal extractor configured to extract emotion signals corresponding to the sensed bio signals by using the emotion changing threshold values;

an emotion signal error state recognizer configured to analyze the peripheral environment signals and the emotion signals to perform error state recognition for each of the emotion signals;

an emotion signal compensator configured to compensate for the recognized error state and optimize the emotion signals according to the error state recognition;

an emotion index inference unit configured to perform emotion inference using the emotion signals and the peripheral environment signals as inputs to infer the emotion index; and an emotion signal information managing unit configured to manage the emotion signals and the emotion index.

10. The sensing device according to claim 1, wherein the emotion signal communication unit includes:

an emotion signal information formatting processor configured to format the emotion signals and provide them to any of a peripheral device, an external authorized device, and an emotion service terminal;

an emotion signal security processor configured to perform a privacy security process for privacy security of the emotional state of the user;

an emotion signal communication protocol processor configured to process protocols for emotion signal communication; and an emotion signal communication matching unit configured to match wireless signals with emotion signals for the emotion signal communication.

11. A method of sensing an emotion signal, the method comprising:

sensing a plurality of bio signals of a user and peripheral environment signals of a user by a sensing signal processor;

generating an emotion signal associated with an emotional state of the user for each of the bio signals sensed by the emotion signal processor and collecting the emotion signals to generate an emotion index; and providing any of the emotion signals and the emotion index to an external authorized device by the emotion signal communication unit, wherein generating the emotion index includes generating error recognition information to recognize an error state based on the peripheral environment signals and the emotion signals, and performing error compensation on each of the emotion signals using the error recognition information.

12. The sensing method according to claim 11, wherein the sensing is performed using at least one of a PPG sensor, a GSR sensor, a temperature/humidity sensor, an acceleration sensor, a voice sensor, and an infrared sensor.

13. The sensing method according to claim 11, wherein the emotion index is generated using the emotion signals and the sensed peripheral environment signals.

14. The sensing method according to claim 11, wherein generating the emotion index includes:

generating the emotion changing threshold values to identify a change in emotion of the user; and extracting emotion signals from corresponding bio signals using the emotion changing threshold values.

15. The sensing method according to claim 11, wherein the emotion index is generated by performing convergence emotion inference using the compensated emotion signals in a multimodal manner.

16. The sensing method according to claim 11, further comprising performing privacy security management and privacy security communication for privacy security for the emotional state of the user before providing the emotion signals or the emotion index to the external authorized device.

* * * * *